(12) United States Patent
Biedermann

(10) Patent No.: US 10,512,493 B2
(45) Date of Patent: *Dec. 24, 2019

(54) BONE PLATE

(71) Applicant: BIEDERMANN TECHNOLOGIES GMBH & CO. KG, Donaueschingen (DE)

(72) Inventor: Markku Biedermann, Miami, FL (US)

(73) Assignee: BIEDERMANN TECHNOLOGIES GMBH & CO. KG, Donaueschingen (DE)

(*) Notice: Subject to any disclaimer, the term of this patent is extended or adjusted under 35 U.S.C. 154(b) by 416 days.

This patent is subject to a terminal disclaimer.

(21) Appl. No.: 15/046,165

(22) Filed: Feb. 17, 2016

(65) Prior Publication Data

US 2016/0235453 A1 Aug. 18, 2016

Related U.S. Application Data

(60) Provisional application No. 62/117,874, filed on Feb. 18, 2015, provisional application No. 62/150,180, filed on Apr. 20, 2015, provisional application No. 62/271,207, filed on Dec. 22, 2015.

(51) Int. Cl.
*A61B 17/80* (2006.01)
(52) U.S. Cl.
CPC .......... *A61B 17/8057* (2013.01); *A61B 17/80* (2013.01); *A61B 17/8042* (2013.01); *A61B 17/8047* (2013.01); *A61B 17/8061* (2013.01)
(58) Field of Classification Search
CPC ............ A61B 17/7044; A61B 17/7058; A61B 17/7059; A61B 17/80; A61B 17/8028; A61B 17/8038; A61B 17/8042; A61B 17/8047; F16B 5/0225
See application file for complete search history.

(56) References Cited

U.S. PATENT DOCUMENTS

| 5,643,265 A * | 7/1997 | Errico ............... A61B 17/7037 606/290 |
| 5,904,683 A * | 5/1999 | Pohndorf ........... A61B 17/7059 606/287 |
| 6,355,038 B1 * | 3/2002 | Pisharodi ........... A61B 17/7043 411/538 |

(Continued)

FOREIGN PATENT DOCUMENTS

| CN | 103040509 A | 4/2013 |
| WO | WO1996032071 A1 | 10/1996 |
| WO | WO2011/150148 A1 | 12/2011 |

OTHER PUBLICATIONS

Extended European Search Report for Application No. EP 16 15 6362, dated Apr. 28, 2016, 8 pages.

(Continued)

*Primary Examiner* — Anu Ramana
(74) *Attorney, Agent, or Firm* — Gordon & Jacobson, P.C.

(57) ABSTRACT

A bone plate is provided including a plate member including a through-hole; a disk provided in the through-hole and rotatably supported in the plate member, the disk including a slot that is shaped such as to allow a guided displacement of the bone plate in a plane perpendicular to an axis of rotation of the disk with respect to a bone anchor extending through the slot.

30 Claims, 13 Drawing Sheets

(56) References Cited

U.S. PATENT DOCUMENTS

| | | | |
|---|---|---|---|
| 7,220,263 B2* | 5/2007 | Cordaro | A61B 17/7059 606/70 |
| 7,766,911 B1* | 8/2010 | Navarro | A61B 17/8047 606/281 |
| 2004/0056167 A1* | 3/2004 | Vogt | F16B 5/0225 248/475.1 |
| 2004/0068319 A1 | 4/2004 | Cordaro | |
| 2004/0127900 A1 | 7/2004 | Konieczynski et al. | |
| 2009/0210067 A1 | 8/2009 | Meridew | |
| 2011/0218533 A1 | 9/2011 | Prandi et al. | |
| 2013/0053898 A1* | 2/2013 | Voisard | A61L 27/34 606/281 |
| 2013/0150900 A1 | 6/2013 | Haddad et al. | |
| 2014/0324108 A1 | 10/2014 | Orbay et al. | |

OTHER PUBLICATIONS

Extended European Search Report for corresponding European Application No. 15184949.4 in the name of Biedermann Technologies GmbH & Co. KG, European Search Report dated Dec. 1, 2015 and dated Dec. 8, 2015 (7 pgs.).

\* cited by examiner

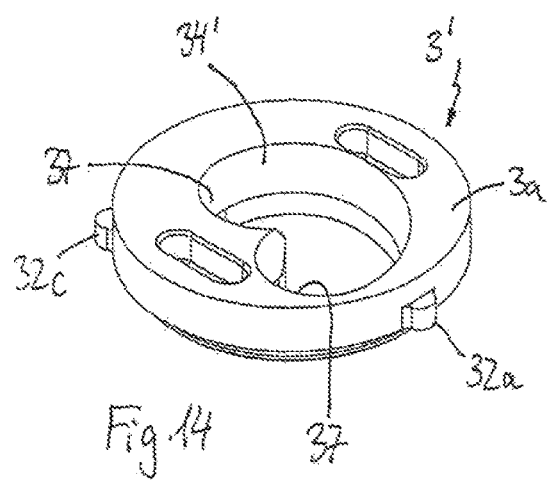
Fig. 14
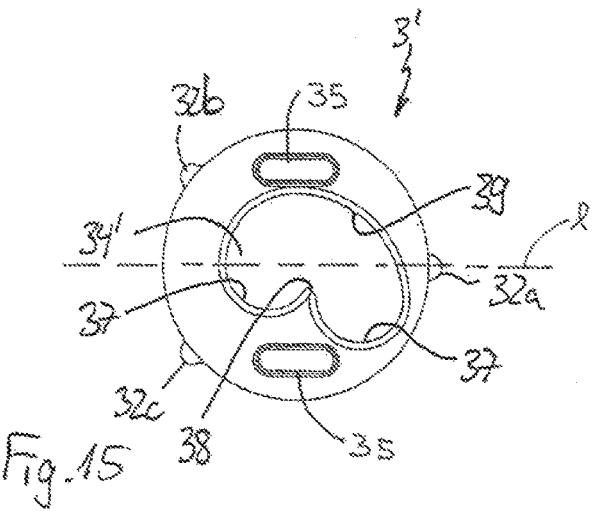
Fig. 15
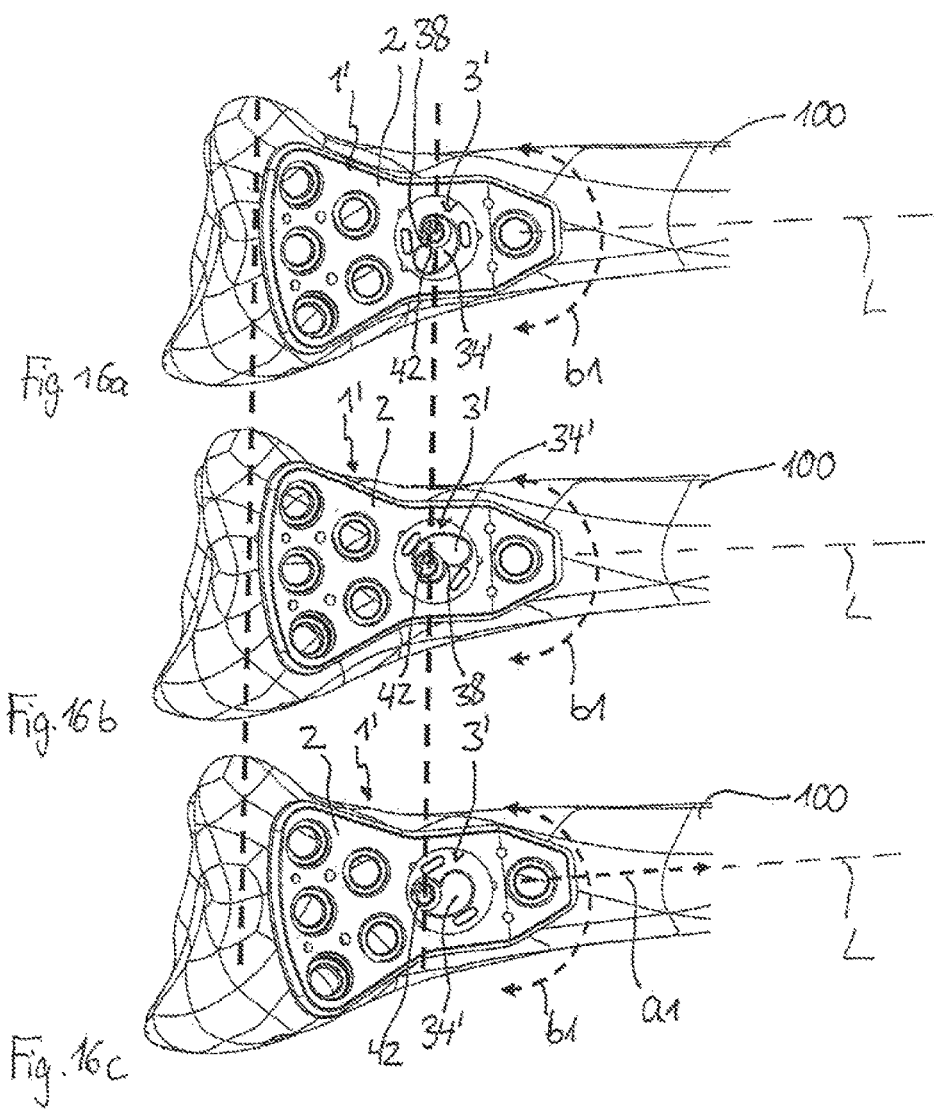
Fig. 16a
Fig. 16b
Fig. 16c

BONE PLATE

CROSS-REFERENCE TO RELATED APPLICATIONS

This application claims the benefit of each of U.S. Provisional Patent Application Ser. No. 62/117,874, filed on Feb. 18, 2015, U.S. Provisional Patent Application Ser. No. 62/150,180, filed on Apr. 20, 2015, and U.S. Provisional Patent Application Ser. No. 62/271,207, filed on Dec. 22, 2015, the entire contents of all of which are hereby incorporated by reference.

BACKGROUND

The invention relates to a bone plate including a plate member with a through-hole and a disk that is rotatably supported in the plate member and extends into the through-hole. The disk comprises a slot that is configured to allow inserting a bone anchor and displacing the bone plate relative to the bone anchor in a guided manner. The bone plate permits alignment and/or reposition of the bone plate after temporary fixation by the bone anchor extending through the slot into the bone.

A bone plate allowing temporary repositioning is described in US 2014/0324108 A1. The bone plate includes a first slot oriented along a longitudinal axis and a slider longitudinally displaceable along the first slot, said slider including a second slot oriented transversely to the longitudinal axis. The bone plate can be longitudinally and rotationally adjusted and in addition permits a temporary repositioning of the bone plate laterally, along an axis transverse to the longitudinal axis.

SUMMARY

According to an aspect of embodiments of the present invention, an improved bone plate allows a simple alignment and/or repositioning of the bone plate once it has been temporarily fixed by a bone anchor, and simultaneously has a high strength under load.

Aspects and features of embodiments of the present invention are described herein with reference to some exemplary embodiments, and are further set forth in the claims.

The bone plate allows alignment, adjustment and/or reposition the bone plate in a multitude of directions that can be selected by linearly displacing the bone plate and/or rotating the disk and displacing the bone plate relative to an inserted bone anchor.

The disk is supported in the plate member and extends across the through-hole. Therefore, the bone plate can be designed without larger openings that may possibly reduce the strength of the bone plate under load. Hence, the bone plate has a high strength.

Because the disk is rotatably supported in the plate member, the disk can be rotated relative to the bone or relative to an inserted bone anchor independently from the plate member. This allows positioning of the disk relative to the plate member in all directions obtainable by rotating the disk in a range of 0° to 360°.

Furthermore, the disk may be provided completely within the through-hole in an axial direction. This results in a low profile of the bone plate.

The disk is loss-proof mounted to the plate member. Thereby the safety of handling of the bone plate is improved. The loss-proof arrangement may be achieved by a design that allows insertion or removal of the disk into or from the plate member only in a certain position of the disk.

A slot is provided in the disk that permits a displacement of the bone plate relative to an inserted bone anchor in a guided manner. The width of the slot is such that the bone plate cannot be removed from the bone as long as the bone anchor is inserted. During displacement, the bone plate is held by the cooperation of the bone anchor and the disk. In one embodiment, the disk has an elongate slot with two long substantially parallel sides that allow a linear displacement of the bone plate relative to an inserted bone anchor along a distance corresponding to the length of the slot. In another embodiment, the disk comprises a spiral-shaped slot that provides a temporary holding of the bone plate in any position along the direction of displacement. Alternative shapes of the slot are conceivable that may provide a guiding function for adjusting and/or repositioning the bone plate.

In a further embodiment, the disk can have an undercut portion that engages a portion of the plate member. By this design the disk is able to take up forces that act on the plate member. The disk may be secured against loss by deforming portions of the disk so that the deformed portions cooperate with portions of the plate member that prevent removal of the disk after mounting.

In a still further embodiment, the bone plate includes a cover member for covering the disk. The cover member may be an optional part. With the cover member, a bone anchor that has been inserted into the slot of the disk may be secured against backing out and/or loss. Moreover, the position of the disk may be fixed with the cover member. With the cover member, the disk remains fixed even if the bone anchor is loosened for some reason. The cover member may also prevent ingrowth of tissue, blood vessels, etc. into the region around the head of the bone anchor. This can be useful in a case where the bone plate is intended to be removed at a later time. Alternatively, empty space of the slot or other portions of the disk may be filled with bone material to improve ingrowth of the bone plate in a case where the bone plate shall stay within the body of the patient.

In a still further embodiment, the disk may be configured to be screwed into the plate member. By means of this, the disk is secured against removal once the disk is inserted into the plate member.

The plate member may have any shape that is suitable for bone plates. In addition, the plate member may have one or more through-holes for accommodating a head of a bone anchor therein for fixing the bone plate to the bone.

In a further aspect, a bone plate assembly is provided that includes the bone plate and a bone anchor, wherein the slot of the disk and the bone anchor are adapted to each other such that the bone plate can perform a guided displacement with respect to the bone anchor inserted into the slot.

According to a still further aspect, a bone plate is provided wherein the through-hole and/or the disk are configured to permit a rotational movement of the plate member relative to the disk only in a limited range of angles. In one embodiment, the disk may have an outer contour that does not match the inner contour of the through-hole in such a manner that at least a portion of the inner wall of the through-hole forms an abutment that limits the rotational movement of the disk. With such a design, the width of the plate member can be reduced. In addition, a total area of the through-hole may be reduced which may increase the strength of the bone plate. The disk may be inserted from the bottom side and may be secured against detachment through the top side of the plate member.

BRIEF DESCRIPTION OF THE DRAWINGS

Further features and advantages of the invention will become apparent from the description of some embodiments by means of the accompanying drawings. In the drawings:

FIG. 14 shows a perspective view from the top of a disk of a bone plate according to another embodiment.

FIG. 15 shows a top view of the disk of FIG. 14.

FIGS. 16a to 16c show first to third positions of the bone plate after temporary fixation to a bone, with the disk of FIG. 14.

DETAILED DESCRIPTION

Figure 1:
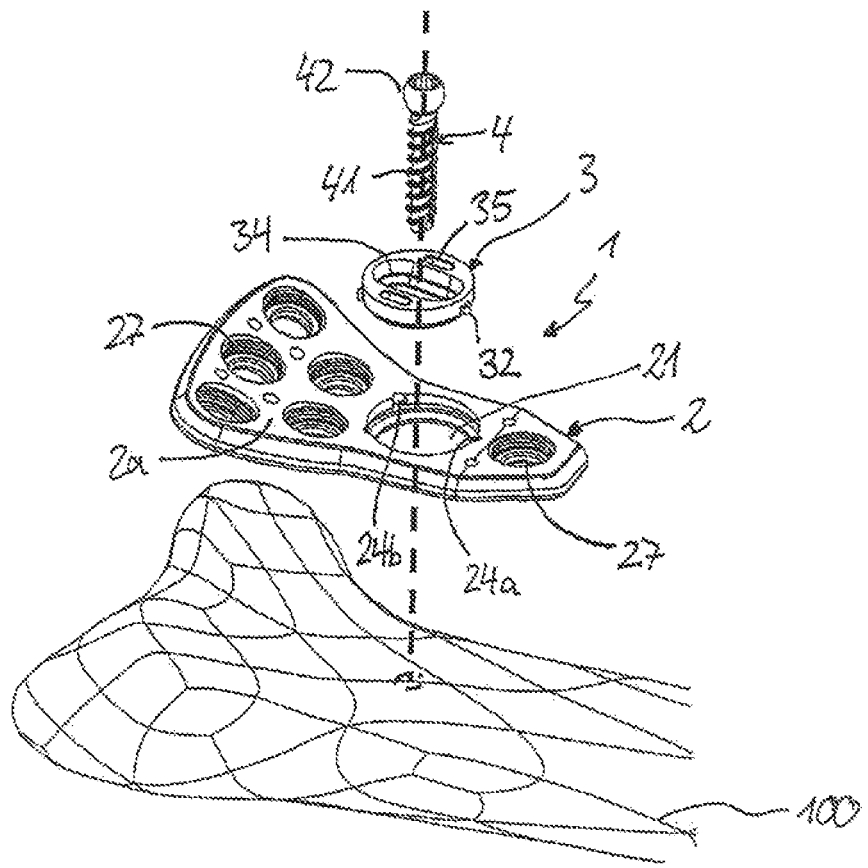
FIG. 1 shows a perspective exploded view of a bone plate with a bone anchor according to an embodiment.
Figure 2:
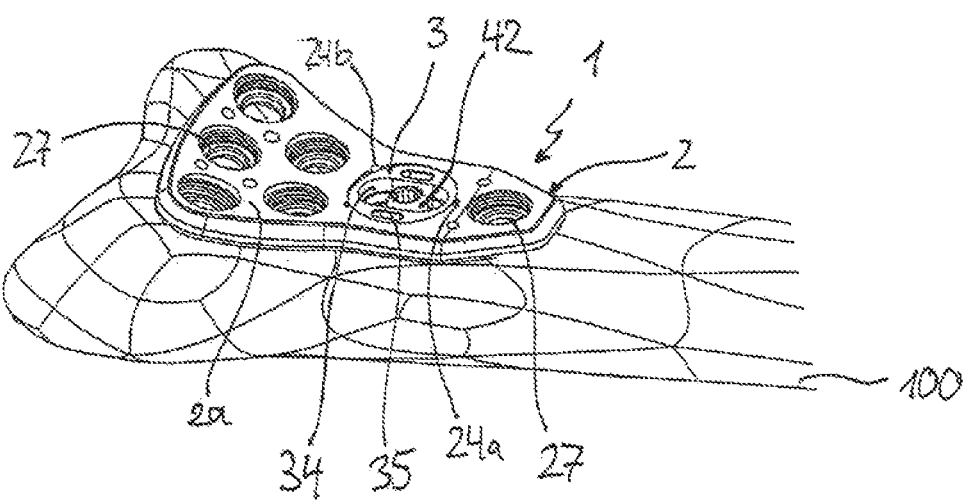
FIG. 2 shows a perspective view of the bone plate with the bone anchor of FIG. 1 attached to a bone.

Referring to FIGS. 1 to 5, a bone plate 1 according to an embodiment includes a plate member 2 and a disk 3 mountable to the plate member 2. The bone plate 1 is configured to be fixed to a bone or a bone part 100 via one or more bone anchors 4. The plate member 2 has a top surface or side 2a and an opposite bottom surface or side 2b. The bottom surface 2b usually includes a bone contacting portion. The shape of the plate member shown is elongate, that means an overall length is greater than an overall width. However, the shape is not limited to an elongate shape. In addition, the plate member 2 may have an angled or bent portion, i.e. may be not completely flat. Alternatively, the plate member 2 may be fully flat. The bone anchor 4 typically includes a shank 41 with a bone engagement structure, such as a bone thread, and a head 42.

Figure 3:
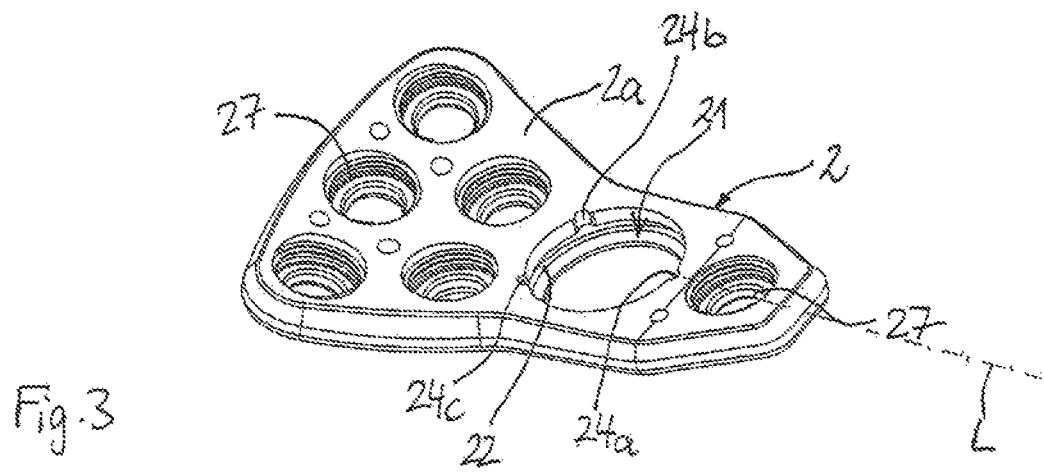
FIG. 3 shows a perspective view from the top of a plate member of the bone plate according to FIGS. 1 and 2.
Figure 4:
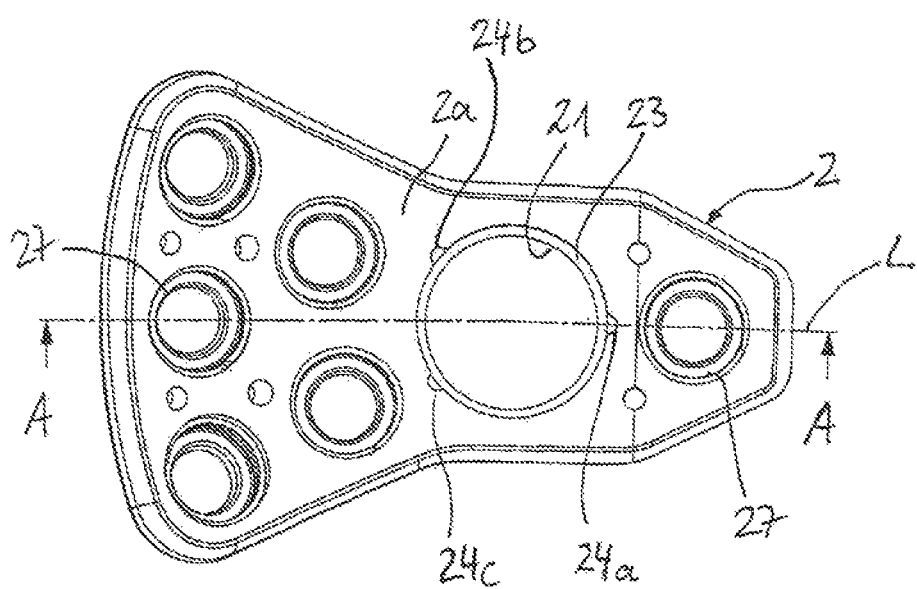
FIG. 4 shows a top view of the plate member of FIG. 3.
Figure 5:
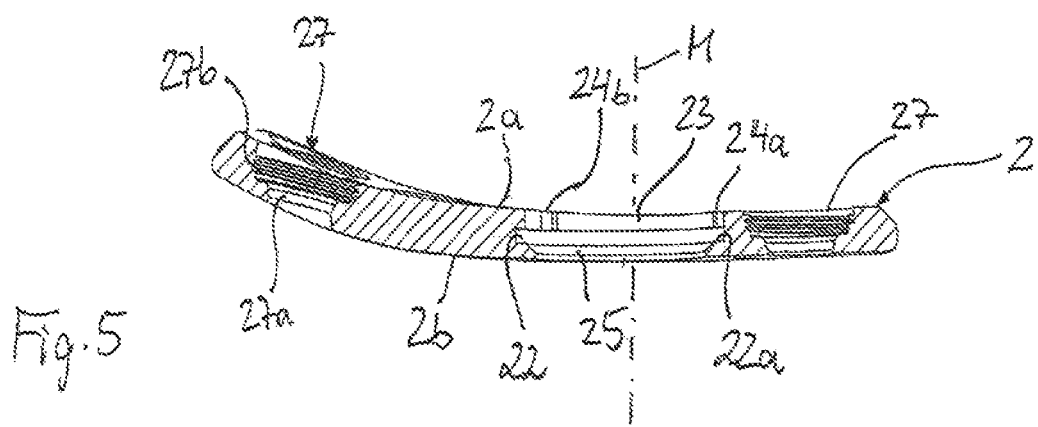
FIG. 5 shows a cross-sectional view of the plate member along line A-A of FIG. 4.

In approximately a central area of the plate member 2 a through-hole 21 is provided that extends completely through the plate member 2 from the top side 2a to the bottom side 2b. The through-hole 21 has such a size that the disk 3 can be accommodated therein. As can be seen in particular in FIG. 5, a central axis M of the through-hole 21 is substantially perpendicular to the top side 2a and the bottom side 2b. In approximately the middle of the plate member 2 in an axial direction, a groove 22 is formed in the inner wall of the through-hole 21. A bottom surface 22a of the groove forms a support surface for the disk 3. Between the groove 22 and the top side 2a, the through-hole 21 comprises an upper portion 23 with an inner diameter that is smaller than an inner diameter of the groove 22 but is the same or slightly larger than an outer diameter of the disk 3. At least one, preferably a plurality, for example three recesses 24a, 24b, 24c, each extends in a radial direction from the upper portion 23 of the through-hole into the plate member 2. As depicted in FIGS. 3 and 4, a first recess 24a is symmetrical to a longitudinal axis L of the plate member 2 and the other two recesses 24b, 24c are provided at an angle with respect to the longitudinal axis L. The recesses 24a, 24b, 24c serve as a guiding structure for the alignment of the disk 3 when the disk 3 is to be inserted. On the side facing towards the bottom side 2b, a lower portion 25 of the through-hole 21 comprises a tapered inner wall that narrows towards the bottom side 2b.

The plate member may have further through-holes 27 each forming an accommodation space for a head of a bone anchor to be inserted. In the embodiment according to FIGS.

1 to 5, the further through-hole 27 may have a seat 27a for supporting a head of a bone anchor and a threaded bore 27b for inserting a locking element (not shown) therein. The plate member may have at least one, preferably a plurality of through-holes 27 for bone anchors. The through-holes 27 may have the same or a different shape. The through-hole 21 for the disk 3 is a single through-hole that has a greater size compared to the other through-holes 27 of the plate member 2.

Figure 6:
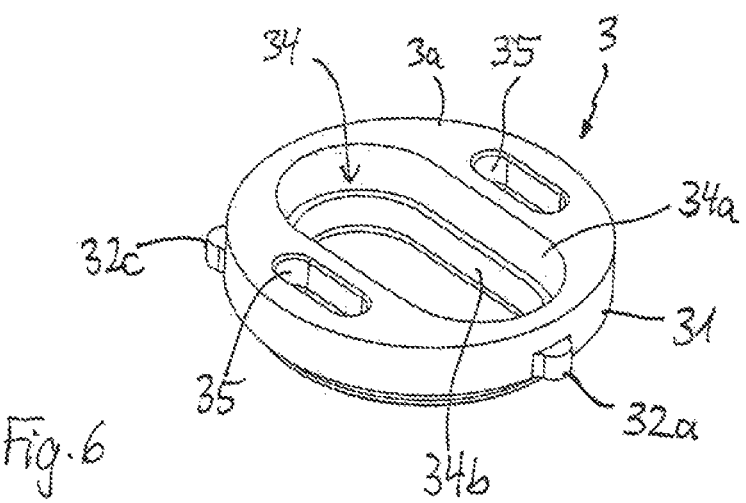
FIG. 6 shows a perspective view from the top of a disk of the bone plate of FIGS. 1 and 2.
Figure 7:
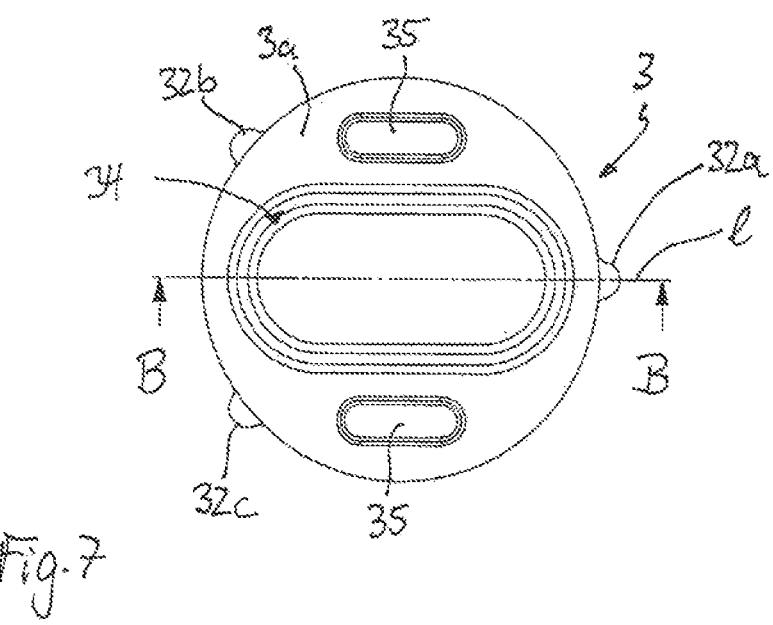
FIG. 7 shows a top view of the disk of FIG. 6.
Figure 8:
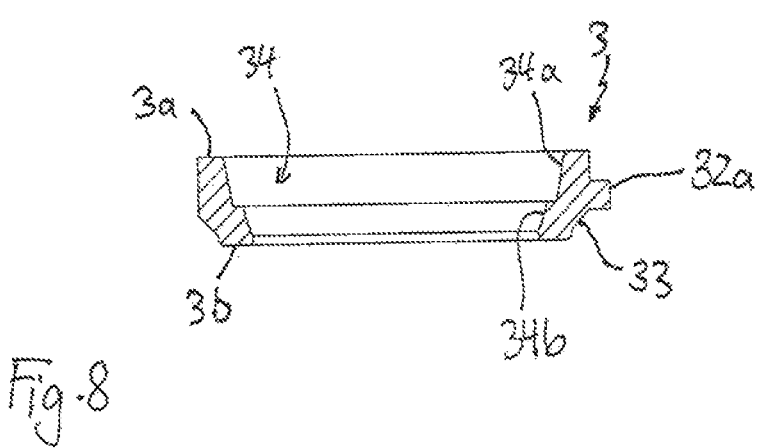
FIG. 8 shows a cross-sectional view of the disk along line B-B in FIG. 7.

As illustrated in FIGS. 6 to 8, the disk 3 has a top side 3a and an opposite bottom side 3b. A first portion 31 including the top side 3a is substantially cylindrical with an outer diameter of the cylinder that is only slightly smaller than an inner diameter of the upper portion 23 of the through-hole 21. Further, a tapered portion 33 is provided that extends from the cylindrical first portion 31 and narrows towards the bottom side 3b. The dimensions of the tapered portion 33 are such that the tapered portion 33 can be seated in the tapered lower portion 25 of the through-hole 21. The tapered lower portion 25 in the through-hole 21 and the tapered portion 33 of the disk 3 provide contact surfaces that allow the disk 3 to seat in the through-hole 21. The tapered shape may render the rotation of the disk 3 smoother. However, the shape of the contact surfaces is not limited to a tapered shape. Any shapes that are matching are possible. One example would be a contact surface that includes a 90° step.

An elongate slot 34 extends completely through the disk 3 from the top side 3a to the bottom side 3b. Two opposite long sides and two opposite short sides form the elongate slot 34. The center of the elongate slot 34 in a longitudinal direction of the elongate slot 34 is arranged substantially at the center of the disk 3. A longitudinal axis l is defined by the orientation of the long sides of the elongate slot 34. At the outer surface of the cylindrical portion 31 at a distance from the top side 3a at least one projection, preferably two or more projections 32a, 32b, 32c project radially outward. The projections may be rounded. One projection 32a is symmetrical to the longitudinal axis l and is provided at an outer surface of the cylindrical portion 31 at one end of the elongate slot 34. Two other projections 32b, 32c may be provided at an angle and symmetrical to the longitudinal axis l on a side of the disk 3 opposite to the first projection 32a. The projections 32a, 32b, 32c are shaped and arranged to cooperate with the recesses 24a, 24b, 24c of the plate member 2.

Adjacent to the top side 3a, the elongate slot 34 comprises a section 34a that widens towards the top side 3a. Between the bottom side 3b and the widening section 34a a seat portion 34b is provided that has a spherical segment-shaped cross-section in a direction perpendicular to the longitudinal axis l. The seat portion 34b is configured to accommodate the head 42 of a bone anchor, preferably a spherically-shaped head. The spherically-shaped seat portion 34b allows insertion of the bone anchor 4 at different angles of the shank 41 with respect to the plate member 2. The width of the elongate slot 34 at a bottom of the seat portion 34b is smaller than the width of the head 42 of the bone anchor 4 but greater than a diameter of the shank 41 so that once the bone anchor 4 has been inserted into the bone, the bone plate 1 is temporarily fixed by the bone anchor 4 and cannot be removed. It shall be noted that the seat portion 34b does not need to be spherically-shaped but can have any other shape that prevents removal of the bone plate 1 after insertion of the bone anchor 4. The elongate slot 34 is configured to provide a guidance for a displacement of the bone plate 1 along the longitudinal axis l relative to the bone anchor 4 once the bone anchor 4 is inserted into the elongate slot 34.

At opposite sides of the long sides of the elongate slot 34 two elongate engagement recesses 35 are provided that extend substantially parallel to the longitudinal axis l. The elongate engagement recesses 35 are configured to be engaged with a tool (not shown) for inserting and/or rotating the disk 3 in the plate member 2.

The plate member 2 and the disk 3 may be made of a biocompatible metal or biocompatible metal alloy, such as stainless steel, titanium, NiTi alloys, such as Nitinol, magnesium or magnesium alloys, or from a biocompatible plastic material, such as, for example, polyether ether ketone (PEEK) or poly-l-lactide acid (PLLA). The plate member 2, the disk 3 and the bone anchors 4 can be made of the same or of different materials.

Figure 9:
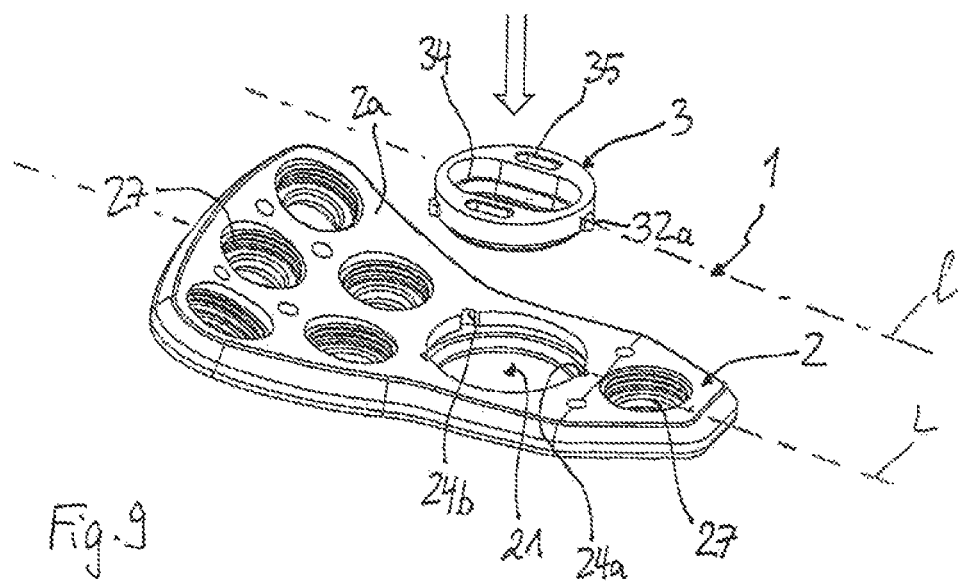
FIG. 9 shows a perspective view of a first step of mounting the disk to the plate member according to an embodiment.
Figure 10:
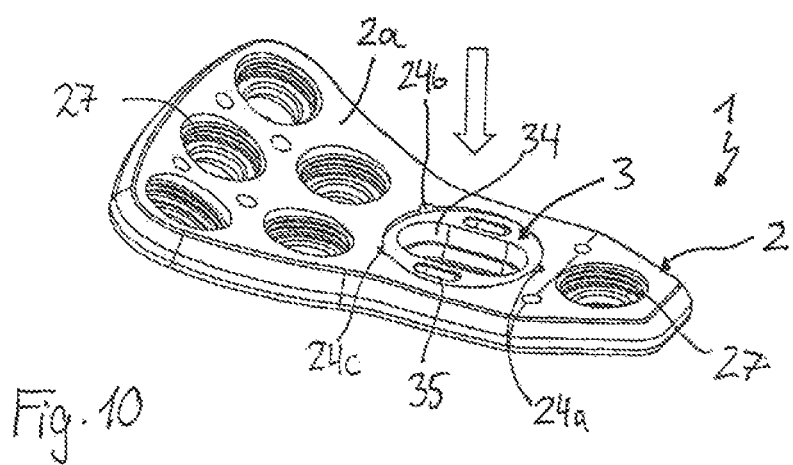
FIG. 10 shows a second step of mounting the disk to the plate member.
Figure 11:
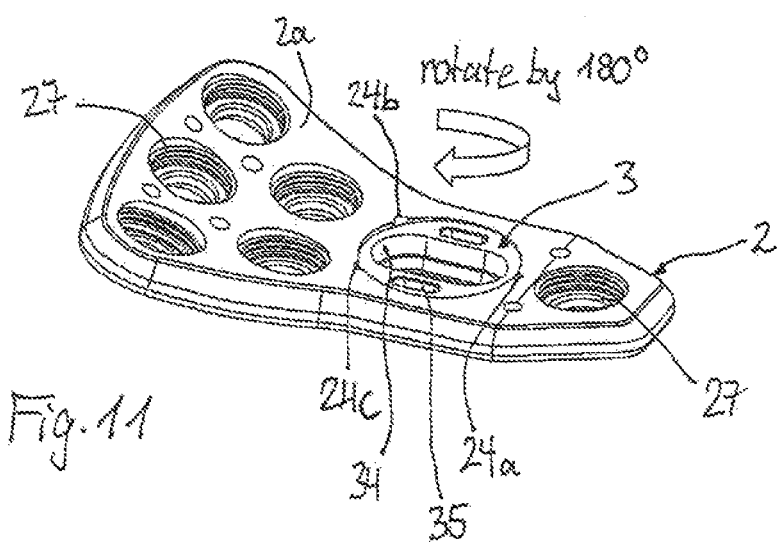
FIG. 11 shows a third step of mounting the disk to the plate member.

Referring to FIGS. 9 to 11, steps of assembly of the bone plate 1 will be described. First, as shown in FIG. 9, the disk 3 is oriented relative to the plate member 2 in such a manner that the bottom side 3b of the disk 3 faces the top side 2a of the plate member 2. Further, the projections 32a, 32b, 32c of the disk 3 are at corresponding positions of the recesses 24a, 24b, 24c of the plate member 2. Aligned in this manner, the disk 3 is then inserted into the through-hole 21 as shown in FIG. 10. Thereby, the projections 32a, 32b, 32c engage the recesses 24a, 24b, 24c. Hence, the disk 3 can be inserted only in a single position where the projections 32a, 32b, 32c engage the recesses 24a, 24b, 24c. When the disk 3 is moved further downward, the projections 32a, 32b, 32c enter the space beneath the recesses 24a, 24b, 24c that is provided by the groove 22. As the bottom 22a of the groove 22 projects into the through-hole 21 with an inner diameter smaller than the outer diameter of the disk 3 at a position of the projections 32a, 32b, 32c, the disk 3 is supported by the support surface 22a in the plate member 2 and can freely rotate.

Thereafter, as illustrated in FIG. 11, the disk 3 is rotated by 180° so that the projections 32a, 32b, 32c are no longer at the positions of the recesses 24a, 24b, 24c. By means of this, the disk 3 is held in the groove 22 of the plate member 2 and cannot be removed. The lower tapered portion 33 of the disk 3 is additionally supported in the tapered lower portion 25 of the through-hole 21. A tool (not shown) may be used to engage the recesses 35 and to rotate the disk 3 in the plate member 2.

Figure 12A:
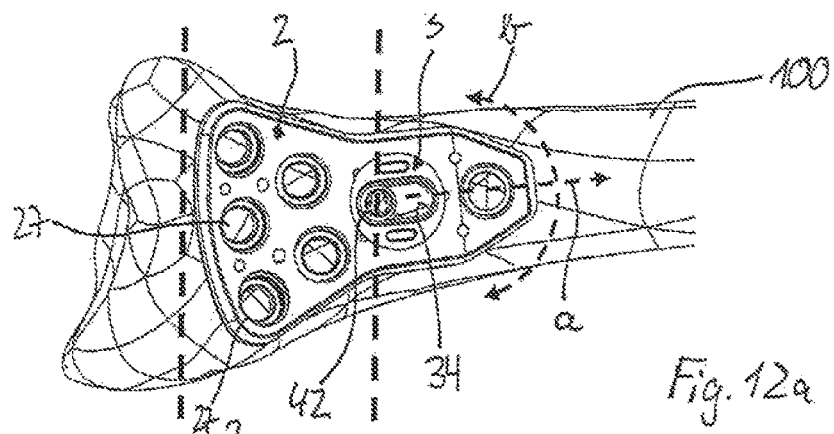
FIG. 12a shows a first position of the bone plate after temporary fixation of the bone plate to the bone.

In use, as depicted in FIGS. 12a to 13b, first, the bone plate 1 is applied to the bone or bone parts 100 that shall be stabilized and/or connected via the bone plate 1. The bone plate 1 may be aligned with respect to the bone 100 such that the longitudinal axis L of the bone plate 1 extends along the longer portion of the bone 100. Then, the bone anchor 4 is inserted into a hole in the bone 100 which may be pre-drilled. At this time, the bone anchor 4 is not fully tightened. The bone anchor 4 is inserted to such a depth in the bone 100 that it temporarily holds the bone plate 1 but still permits a displacement of the bone plate 1 along the longitudinal axis l of the elongate slot 34 relative to the bone anchor 4. In more detail, the head 42 of the bone anchor 4 is seated in the seat portion 34b of the elongate slot 34 but does not completely fix the bone plate 1 to the bone 100, otherwise the bone plate 1 would compress the bone 100 and movement of the bone plate 1 would not be possible. Once the bone anchor 4 has been inserted in the bone 100, the position of the bone plate 1 can be adjusted in several ways. In FIG. 12a, the bone plate 1 is shifted to the right side as shown by the arrow a until the head 42 of the bone anchor 4 is at the outermost left end of the elongate slot 34. Simultaneously, the bone plate 1 may be rotated around the temporarily fixed bone anchor 4 by rotation as shown by the double arrows b.

The dashed vertical lines shall illustrate fixed positions on the bone 100. The change of the position of the bone plate 1 relative to the bone 100 can be seen in relation to these vertical dashed lines.

Figure 12B:
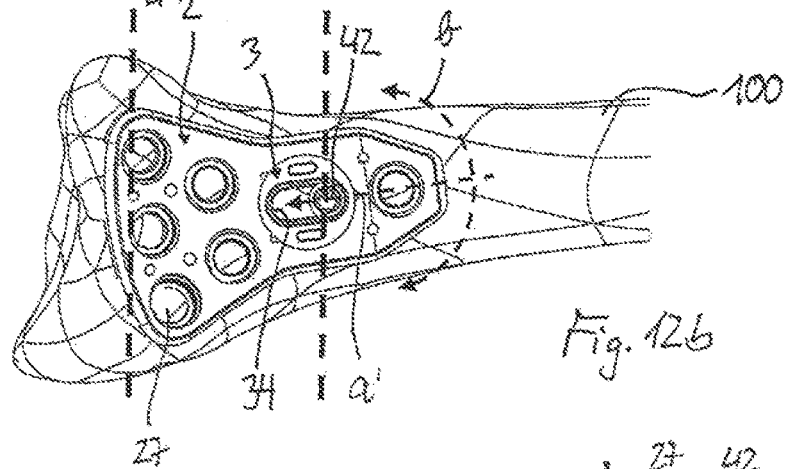
FIG. 12b shows a second position of the bone plate after temporary fixation of the bone plate to the bone.

As depicted in FIG. 12b, the bone plate 1 may be moved to the left side as shown by the arrow a' until the head 42 of the bone anchor 4 abuts against the outermost right end of the elongate slot 34. Simultaneously, the bone plate 1 can be rotated around the bone anchor in the direction of the double arrows b. As can be seen in FIGS. 12a and 12b, in a longitudinal direction along the longitudinal axis L of the bone plate, the position of the bone plate can be corrected and/or adjusted in a range corresponding to the length of the elongate slot 34. The bone plate 1 may also be adjusted to assume any intermediate position between the two end positions shown and may be also rotated in this position. During displacement, the bone plate 1 is guided by the elongate slot 34.

Figure 13A:
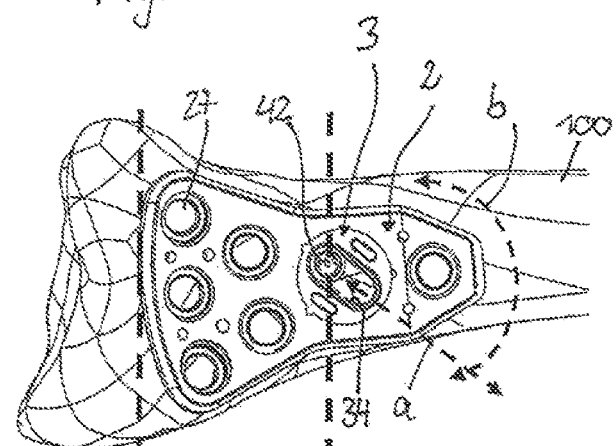
FIG. 13a shows a third position of the bone plate after temporary fixation to the bone, with the disk rotated relative to the plate member.
Figure 13B:
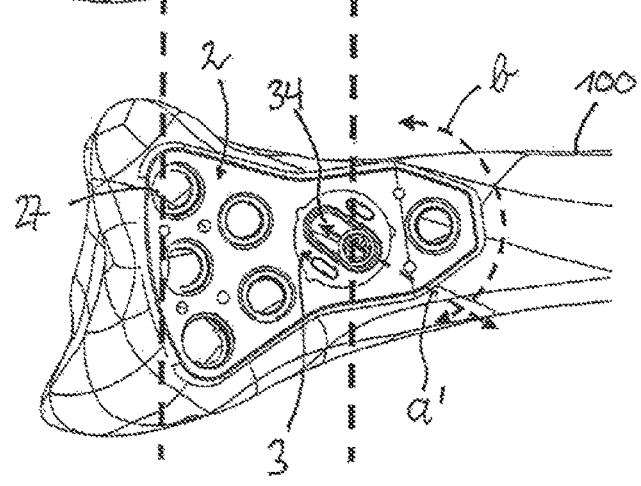
FIG. 13b shows a fourth position of the bone plate after temporary fixation to the bone, with the disk rotated relative to the plate member.

Additionally, as depicted in FIGS. 13a and 13b, the disk 3 may be rotated in advance or during the adjustment or repositioning procedure using a tool (not shown) so that the longitudinal axis l of the elongate slot 34 assumes an angle with respect to the longitudinal axis L of the plate member 2, for example 45° or any other angle. With the disk 3 rotated as shown, the bone plate 1 can be displaced such that the bone anchor 4 is positioned at the outermost left end (FIG. 13a) or at the outermost right end (FIG. 13b) of the elongate slot 34 or at any intermediate position. Simultaneously, the bone plate 1 can be rotated around the bone anchor 4 in the direction of the double arrows b, respectively. A plurality of positions of the bone plate 1 relative to the bone 100 can be obtained using a combination of linear displacement and rotation of the bone plate 1. The rotation can be a rotation of the plate member 2 and the disk 3 together around the inserted bone anchor 4 or independent rotation of the disk 3 relative to the plate member 2 around the inserted bone anchor 4.

When the optimum position of the bone plate 1 relative to the bone 100 is found, the bone anchor 4 extending through the slot 34 is fully tightened and one or more further bone anchors 4 may be inserted into the bone plate 1 through the other through-holes 27. When all necessary bone anchors 4 are inserted and fully tightened, the bone plate 1 is fixed to the bone 100.

By the possibility of adjusting and repositioning the bone plate 1, the bone plate 1 can be more precisely placed at the correct position. In particular, if the bone plate 1 is not fully flat but slightly angled in at least a portion thereof, or in the case of a complicated operation site, the procedure allows a more simplified placement.

Turning now to FIGS. 14 to 16c, another embodiment of a bone plate 1' will be described.

The bone plate 1' differs from the previous embodiment by the design of a disk 3'. The disk 3' differs from the disk 3 of the previous embodiment only in the shape of a slot 34'. All other parts of the disk 3' and the plate member 2 are identical or highly similar to that of the first embodiment and the description thereof will not be repeated. The slot 34' has a curved contour. In more detail, the inner contour of the slot 34' resembles a spiral with a width. The shape can be obtained by cutting a circular area in such a manner that the centerpoint of the circle moves along a spiral path. Thereby, two end portions 37 are formed that are separated from each other by a ridge 38. The slot 34' has a curved long side 39 opposite to the ridge 38. This specific shape of the slot 34' allows the bone plate to be held in any position between the end portions 37. The orientation of the slot 34' is such that the ridge 38 points in a direction substantially perpendicular to the longitudinal axis l which is in this case defined by the projections 32a, 32b, 32c and the engagement recesses 35.

The use of the bone plate 1' is shown in FIGS. 16a to 16c. In order to displace the bone plate 1' along the slot 34', the disk 3' has to be rotated. In FIG. 16a, the disk 3' is positioned in such a manner, that the ridge 38 points approximately in the direction of the longitudinal axis L of the plate member 2. The head 42 of the bone anchor 4 is in the upper one of the end portions 37. The bone plate can additionally be rotated around the bone anchor 4 in the direction of the double arrow b1.

FIGS. 16b and 16c depict two further rotational positions of the disk 3' relative to the plate member 2. With the rotation of the disk 3', the bone plate 1' is displaced as can be seen from the position of the bone plate 1' relative to the dashed vertical lines. The bone plate 1' can additionally be rotated along the double arrow b1 (FIG. 16b) and b1 (FIG. 16c). In this embodiment, displacement of the bone plate 1' and rotation of the disk 3' relative to the bone 100 or the inserted bone anchor 4 are dependent from each other. Therefore, the bone plate 1' is guided in such a manner that it cannot be moved inadvertently out of a certain position.

Figure 17:
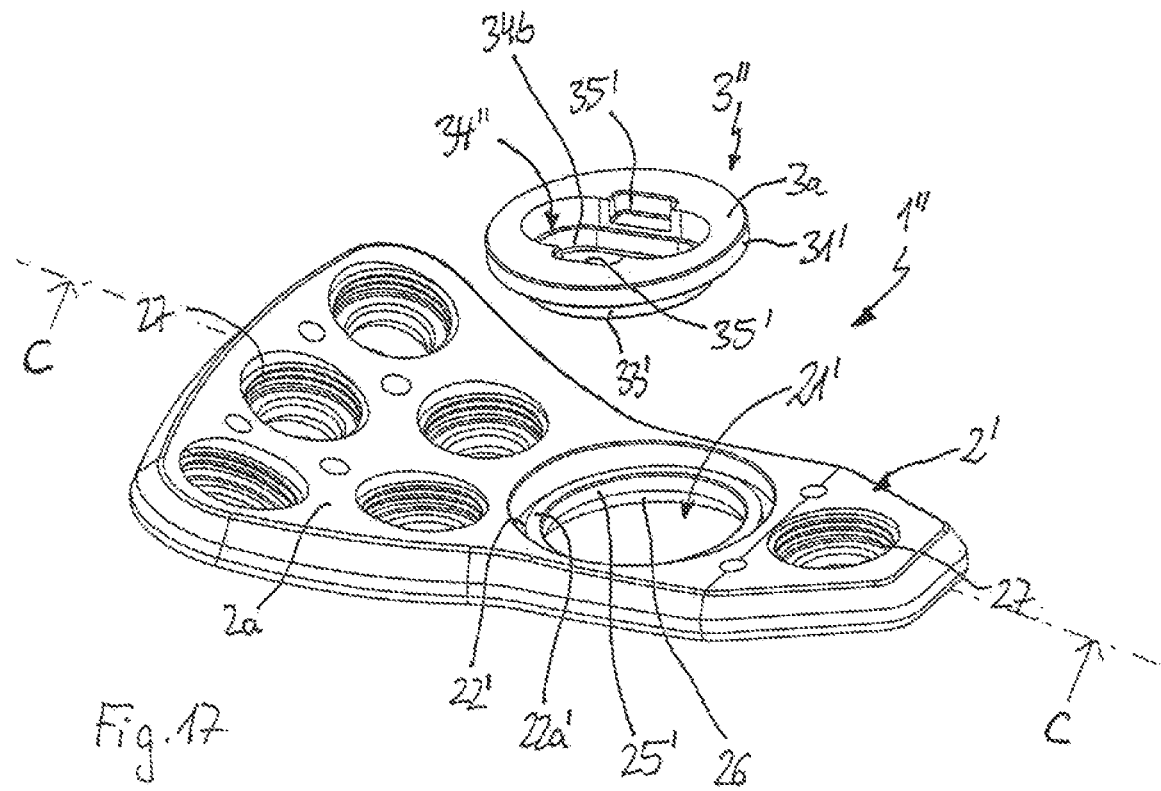
FIG. 17 shows a perspective exploded view of a bone plate according to another embodiment.
Figure 18:
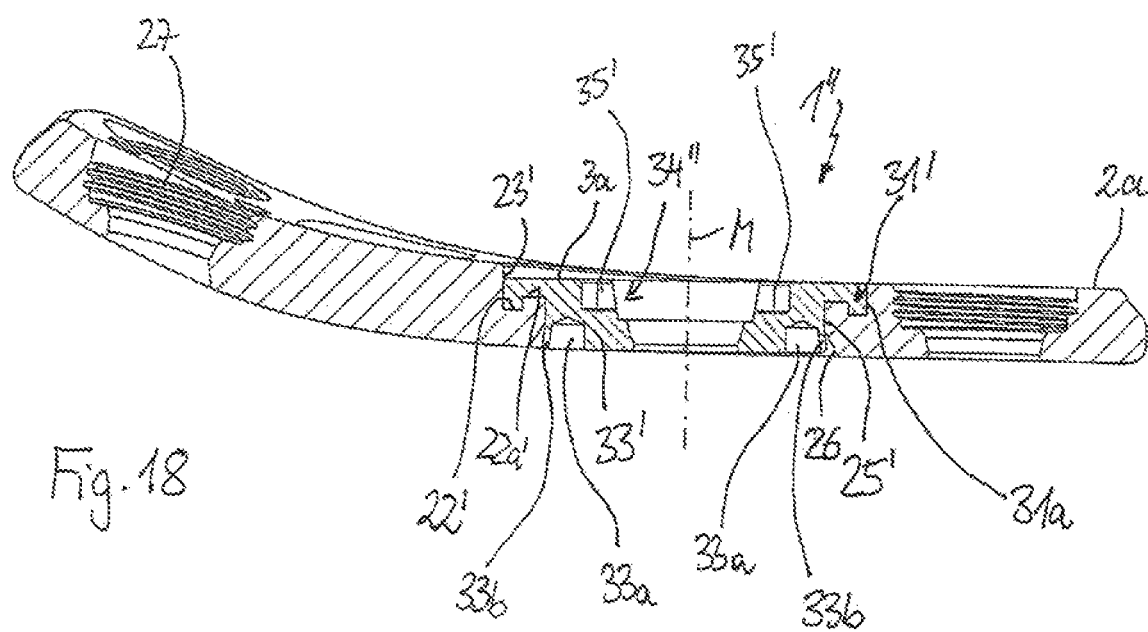
FIG. 18 shows a cross-sectional view of the bone plate of FIG. 17 in an assembled state along line C-C in FIG. 17.

Another embodiment of a bone plate 1" will be described with reference to FIGS. 17 and 18. The bone plate 1" differs from the bone plates of the previous embodiments in the design of a through-hole 21' and a disk 3". The through-hole 21' of a plate member 2' comprises an upper first portion 23' with an inner diameter that matches a largest outer diameter of the disk 3". A bottom of the first portion 23' comprises a groove 22' that is separated from the inside of the through-hole 21' by an annular rim 22a'. The first portion 23' of the through-hole 21' continues to a cylindrical portion 25' of the through-hole 21' that continues to a conically-shaped portion 26 that widens towards the bottom side 2b of the plate member 2'.

The disk 3" has adjacent to the top side 3a a first cylindrical portion 31' with an outer flange 31a that is sized and shaped to engage the groove 22' and the annular rim 22a'. The groove 22' and the annular rim 22a' form a support surface for the disk 3". The disk 3" further comprises a lower portion 33' that is substantially cylindrical and extends up to the bottom side 2b of the plate member 2' when the disk 3" is inserted into the plate member 2'. A pair of blind bores 33a is provided in the bottom side 3b of the disk 3" close to the outer wall of the cylindrical lower portion 33'. A wall portion 33b between each of the blind bores 33a and the outer surface of the disk is a thin portion which is configured to be slightly deformed when a tool is applied that widens the blind bore 33a.

An elongate slot 34" of the disk 3" is identical or highly similar to the elongate slot 34 of the disk 3 described above. In the disk 3", however, engagement recesses 35' extend into the elongate slot 34" as depicted in FIG. 17. This facilitates the engagement by a tool.

The disk 3" is assembled as follows. A tool is used to engage the engagement recesses 35'. Such a tool may have two arms that are spread apart by a spring so that the arms of the tool can engage and be spread apart into the recesses 35'. The disk 3" is inserted into the through-hole 21' so that the flange 31a engages the groove 22' and the annular rim 22a'. Thereafter, a tool, such as, for example, a conical die is inserted into the blind bores 33a such that the wall portions 33b are deformed outward. By means of this, the wall portions 33b engage the conically widening portion 26 of the through-hole 21' and prevent a removal of the disk 3". The disk 3" can then be rotated within the through-hole 21' to a desired rotational position. Depending on the amount of deformation of the wall portions 33b, it is possible to hold the disk 3" in the plate member 2' in a certain rotational position by friction between the disk 3" and the plate member 2'. The rotational position of the disk 3" can be changed by overcoming the frictional force.

Due to the engagement of the outer flange 31a with the groove 22' and the annular rim 22a', the disk 3" is configured to take up forces that act on the bone plate 1" during use of the bone plate 1". The disk 3" can be manufactured in a simple manner.

Another embodiment of a bone plate 1''' will be described with reference to FIGS. 19 to 26. The bone plate 1''' differs from the bone plates of the previous embodiments in the design of a through-hole 21" and a disk 3'''. All other parts and portions are identical or highly similar to the corresponding parts and portions of the previous embodiments and the description thereof will not be repeated. As depicted in particular in FIGS. 19 and 20, the through-hole 21" formed in a plate member 2" has an elongate shape, more specifically a substantially oblong shape with two opposite straight long sides 21a and two opposite convexly rounded short sides 21b. As can be seen in particular in FIGS. 19 and 24, a groove 22" is formed in an inner wall of the through-hole 21" in the region of the short sides 21b. The bottom surface 22a of the groove 22" forms at least a portion of a support surface for the disk 3''' of this embodiment. On the side facing towards the bottom side 2b of the plate member 2", a lower portion 25" of the through-hole 21" comprises a tapered inner wall portion 25" that narrows towards the bottom side 2b as particularly shown in FIGS. 19 and 24. The tapered inner wall portion 25" is present in the region of the short sides 21b and forms a further support surface for the disk 3'''. It shall be noted that any other shape of the lower portion that provides support for the disk 3''' may also be used. An upper portion 23" of the through-hole 21" has a width in the direction of the longitudinal axis L of the plate member 2" that is smaller than an inner diameter of the groove 22" but slightly larger than a length of the disk 3''' in the longitudinal direction. At least one, preferably two opposite recesses 24a", each extend through the tapered inner wall portion 25". The recesses 24a" are arranged in a plane containing the longitudinal axis L. The purpose of the recesses 24a" is to provide a guiding structure for alignment and insertion of the disk 3'''.

Figure 21:
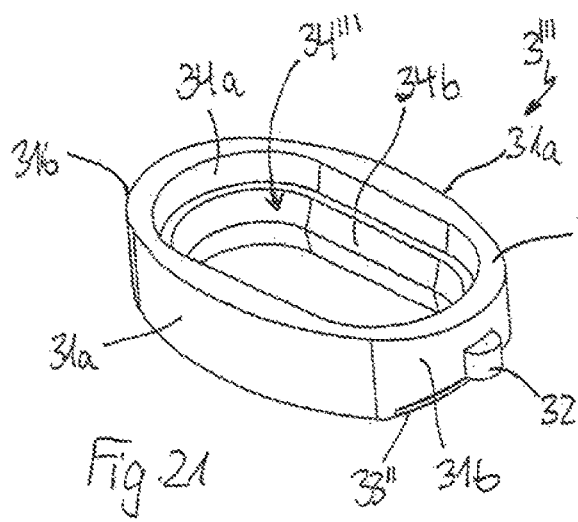
FIG. 21 shows a perspective view from above of a disk of the bone plate according to FIGS. 19 and 20.
Figure 22:
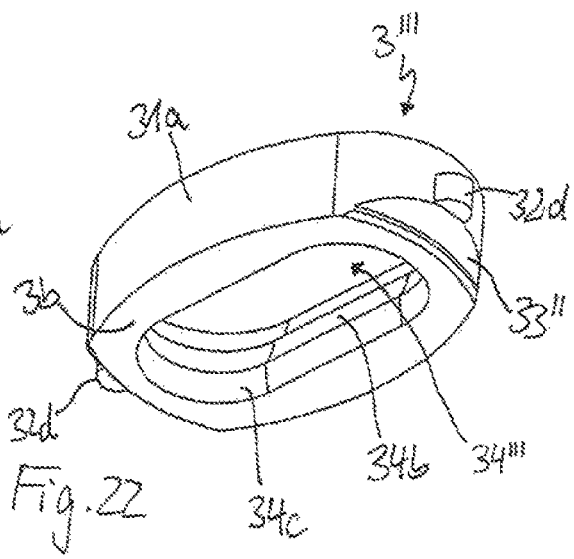
FIG. 22 shows a perspective view from the bottom of the disk of FIG. 21.
Figure 23:
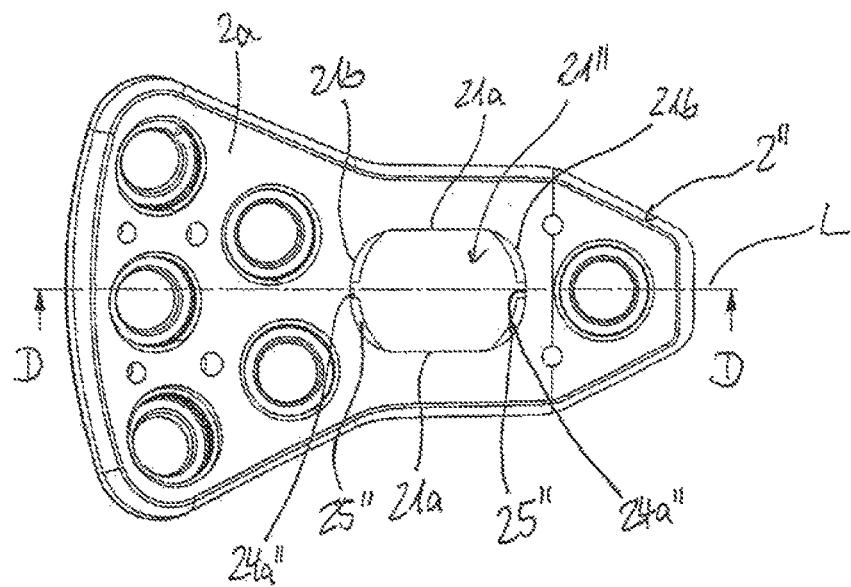
FIG. 23 shows a top view of a plate member of the bone plate of FIGS. 19 and 20.
Figure 24:
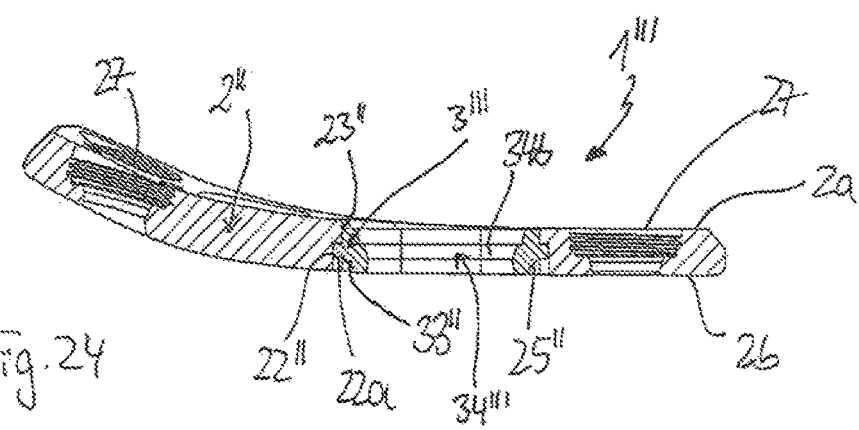
FIG. 24 shows a cross-sectional view of the plate member with inserted disk along line D-D in FIG. 23.
Figure 25:
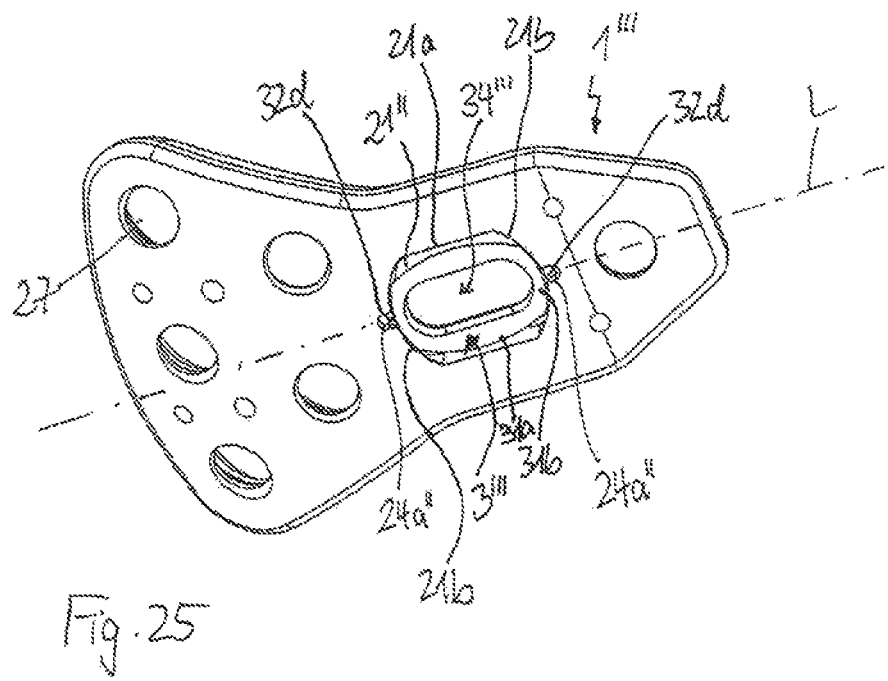
FIG. 25 shows a perspective view from the bottom of the bone plate according to FIGS. 19 and 20.

Turning now to FIGS. 21 and 22, the disk 3''' has a substantially elongate shape comprising opposite long sides 31a and opposite short sides 31b. The short sides 31b have a substantially cylinder segment-shaped outer shape. The long sides 31a may be convexly rounded. At the outer surface of the short sides 31b two opposite projections 32d are provided that are configured to engage the recesses 24a" of the through-hole 21" and to rest on the support surface 22a of the groove 22" of the through-hole 21" once the disk 3''' has been inserted and rotated in the through-hole 21". On the short sides 31b, below the projections 32d, a tapered portion 33" is provided on each side. The tapered portion 33" is configured to cooperate with the tapered portion 25" in the through-hole 21". Instead of the tapered portion 33" any other shape may be used that is configured to be supported by a corresponding support surface provided in the through-hole 21". The height of the disk 3''' is such that after insertion, the disk 3''' is completely in the through-hole 21" or only minimally projects out of the top side 2a or the bottom side 2b of the plate member 2".

Figure 26:
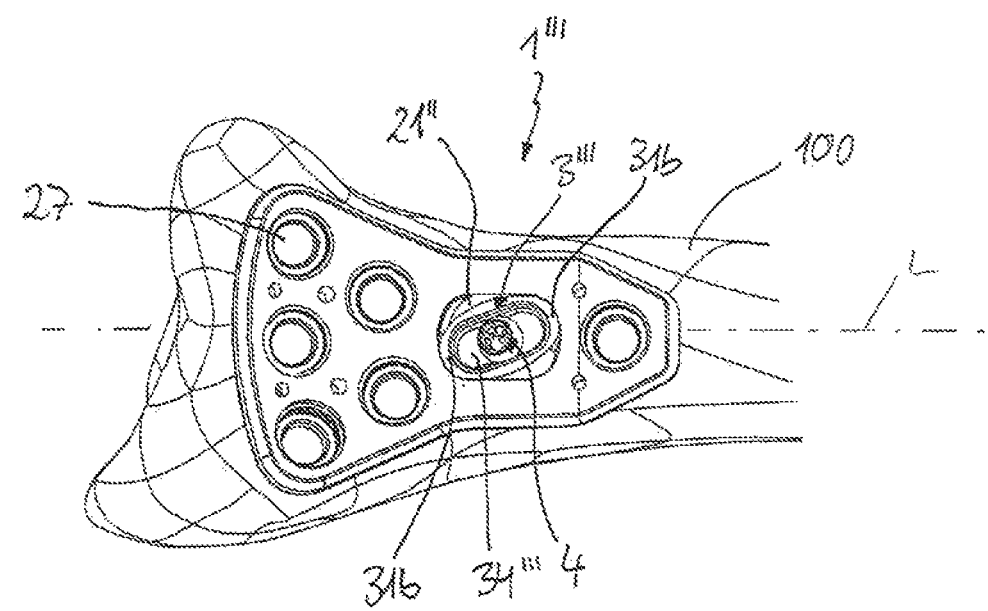
FIG. 26 shows a perspective view from the top of the bone plate according to FIGS. 19 to 25 applied to a bone with a bone anchor.

The disk 3''' has such a length in the longitudinal direction that the disk 3''' is insertable into the through-hole 21" of the plate member 2" with the projections 32d engaging the recesses 24a". In the inserted state, the short sides 31b of the disk 3''' are spaced apart only slightly from the inner wall of the short side 21b of the through-hole 21". The outer width of the disk 3''' in a direction perpendicular to the longitudinal direction is smaller than the width of the through-hole 21" in this direction. When the disk 3''' is rotated within the through-hole 21", it can be rotated only until it abuts against one of the long sides 21a of the through-hole 21" as depicted in FIG. 26. Hence, the rotation is limited by an abutment provided by an inner wall portion of the through-hole 21". More generally, an outer shape of the disk 3''' and an inner shape of the through-hole 21" are non-matching in such a manner that an abutment is provided that limits the rotation of the disk 3'''. The lateral space between the disk 3''' and the inner wall of the through-hole 21" may also be used for applying an instrument to rotate the disk 3'''.

The disk 3''' further comprises an elongate slot 34''' that is substantially the same as the elongate slot 34 of the disk 3 described above, with the upper portion 34a, the seat portion 34b for the head 42 of the bone anchor 4, and a lower portion 34c that widens towards the bottom side 3b.

Figure 19:
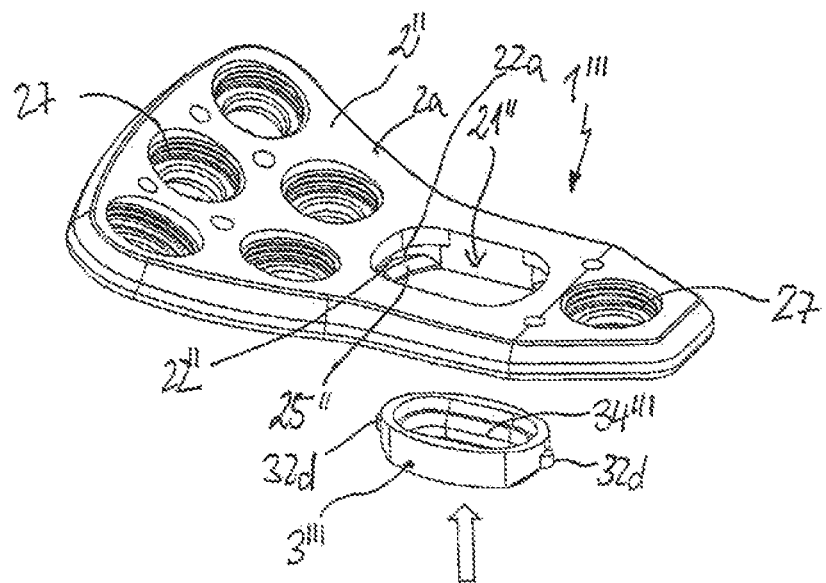
FIG. 19 shows a perspective exploded view of a bone plate according to another embodiment.
Figure 20:
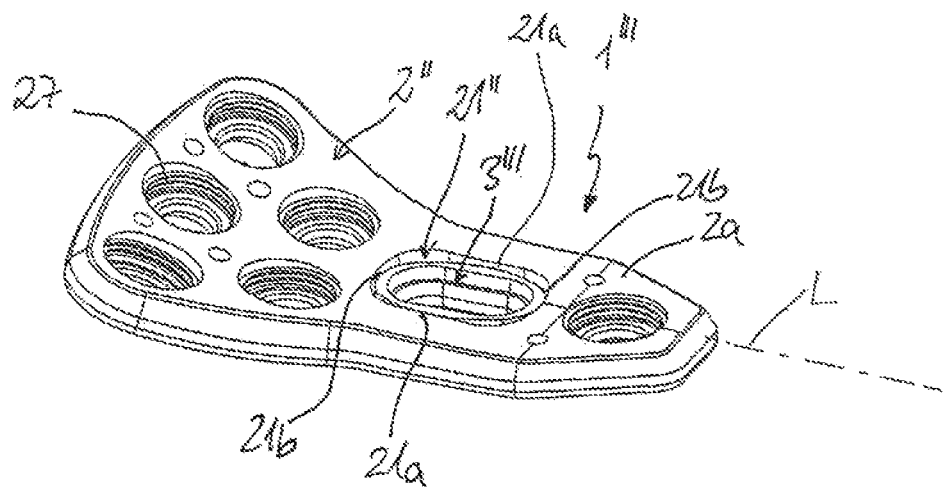
FIG. 20 shows a perspective view of the bone plate of FIG. 19 in an assembled state.

As depicted in FIG. 19, the disk 3''' can be inserted from the bottom side 2b of the plate member 2". To accomplish this, the disk 3''' is orientated such that the projections 32d are aligned with the recesses 24a". Once the disk 3''' has been inserted, it is rotated so that the projections 32d engage the groove 22" and until the short sides 31b of the disk 3''' abut against the inner edges of the elongate through-hole 21". In the present embodiment the dimensions are such that the disk 3''' can be rotated until it lies in the diagonal extending across the oblong through-hole 21". The angular range of rotation for the disk 3''' may be, for example, approximately ±10 to 15 degrees measured from the longitudinal axis L. By changing the shapes and/or dimensions, specific angular ranges may be realized. Once it is rotated, the disk 3''' is held in the plate member 2" and cannot fall out.

Use of the bone plate 1" is similar to the previous embodiments. After the plate member 2" has been preliminarily fixed by the bone anchor 4 as depicted in FIG. 26, a position of the plate member 2" can be adjusted by rotating and/or displacing the plate member 2" relative to the inserted bone anchor 4. Furthermore, by rotating the disk 3''' relative to the plate member 2", further degrees of freedom of positioning of the plate member 2" relative to the bone anchor 4 can be achieved. Since the disk 3''' is held by the projections 32d in the groove 22" It cannot be detached from the plate member 2" through the top side 2a.

With the elongate shape of the through-hole 21" and the disk 3''', a slim design of the plate member 2" may be realized. Thus, the width of the plate member 2" can be made very small for particular applications, such as in cervical, pediatric, or hand surgery. At the same time, the area of the through-hole 21" relative to the total area of the plate member 2" can be reduced, which enhances the mechanical strength of the bone plate 1'''.

Another embodiment of a bone plate 101 will be described with reference to FIGS. 27 to 35. The bone plate 101 differs from the bone plates of the previous embodiments in the design of a through-hole 210 and a disk 300. All other parts or portions are identical or highly similar to the corresponding parts and portions of the previous embodiments and the description thereof will not be repeated. As depicted in particular in FIGS. 27 and 28, the bone plate 101 includes a plate member 201, the disk 300, and a cover member 500. As shown more in detail in FIGS. 29 and 30, the through-hole 210 comprises a substantially cylindrical non-threaded portion 220 with a bottom 220a that is located between the top surface 2a and the bottom surface 2b of the plate member 201. A threaded portion 221 with an internal thread is provided between the top surface 2a and the non-threaded portion 220. The internal thread may consist of only a single thread turn or even a portion of a thread turn, or of several thread turns. Moreover, the internal thread may reach up to the top side 2a of the plate member 201. The non-threaded portion 220 comprises an inner diameter that is at least as large as the thread diameter of the internal thread of the threaded portion 221. From the bottom 220a, a lower portion 250 of the through-hole 210 comprises a tapered inner wall that narrows towards the bottom side 2b of the plate member 201.

Further through-holes 27, 27' of various sizes may be provided, as in the previous embodiments. The through-hole 210 for the disk 300 is a single through-hole that has a greater size compared to the other through-holes 27, 27' of the plate member 201.

Figure 27:
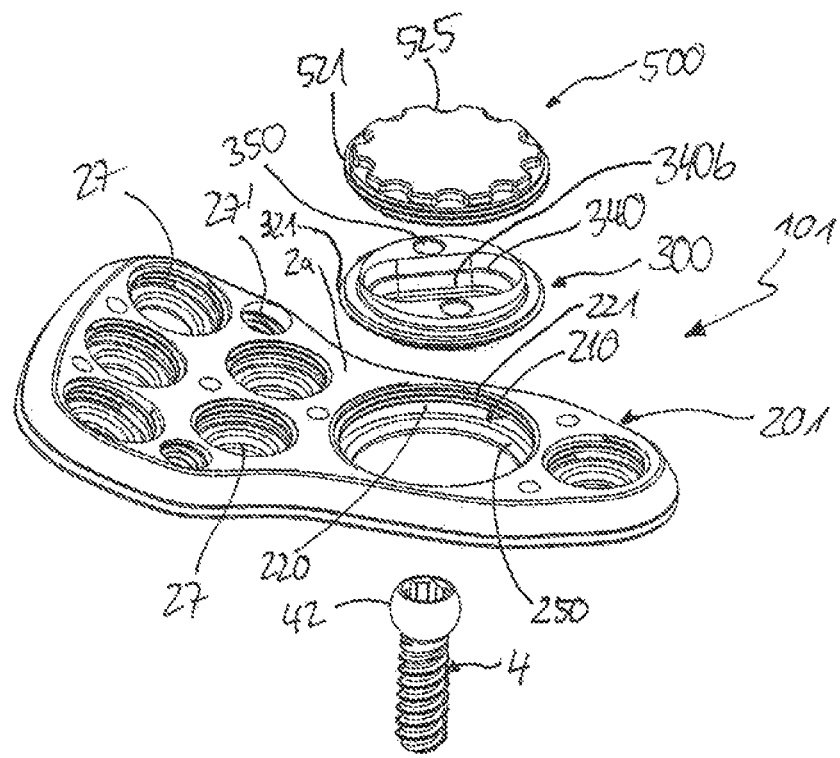
FIG. 27 shows a perspective exploded view of a bone plate with a bone anchor according to another embodiment.
Figure 28:
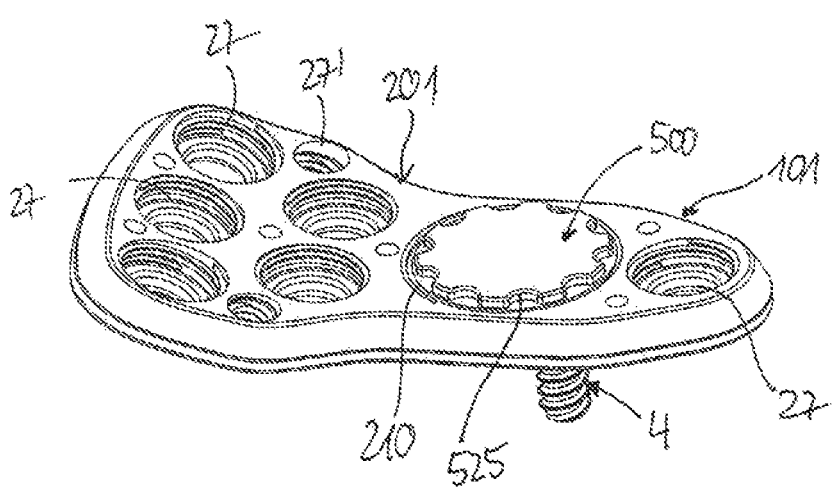
FIG. 28 shows a perspective view of the bone plate of FIG. 27 in an assembled state.
Figure 29:
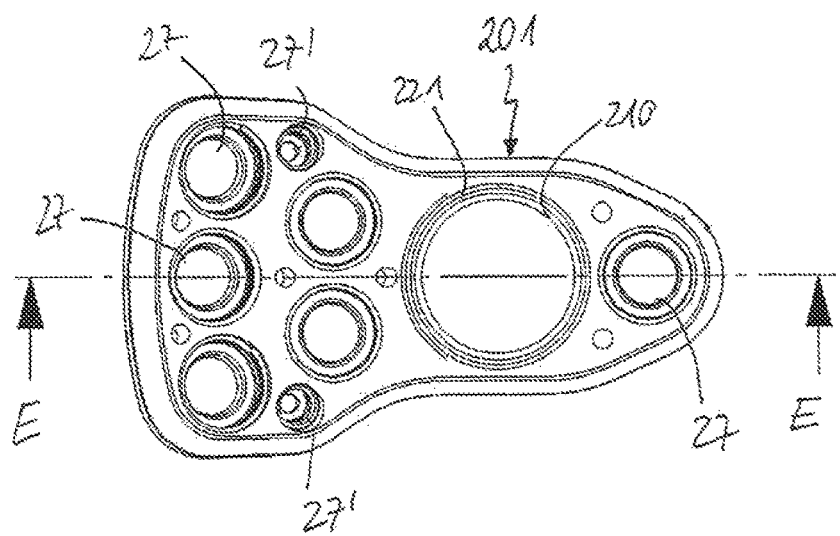
FIG. 29 shows a top view of a plate member of the bone plate of FIGS. 27 and 28.
Figure 30:
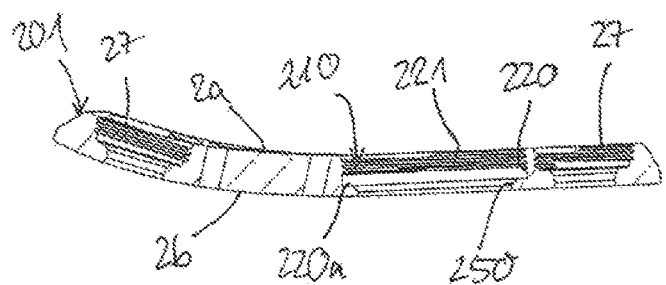
FIG. 30 shows a cross-sectional view of the plate member of FIG. 27 to 29 along line E-E in FIG. 29.
Figure 31:
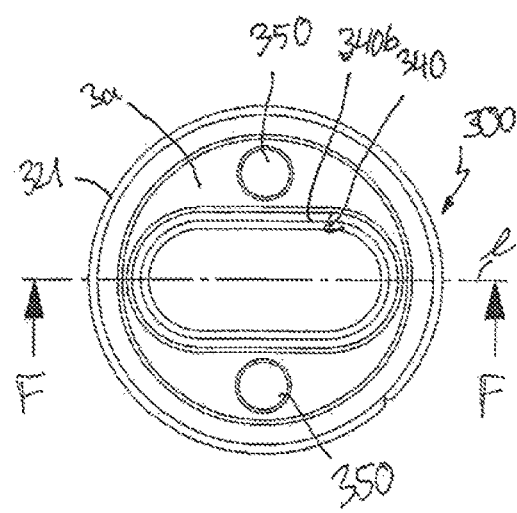
FIG. 31 shows a top view of a disk of the bone plate shown in FIGS. 27 and 28.
Figure 32:
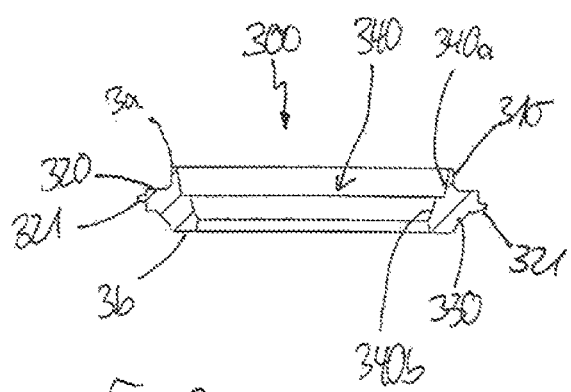
FIG. 32 shows a cross-sectional view of the disk of FIG. 31 along line F-F in FIG. 31.
Figure 33:
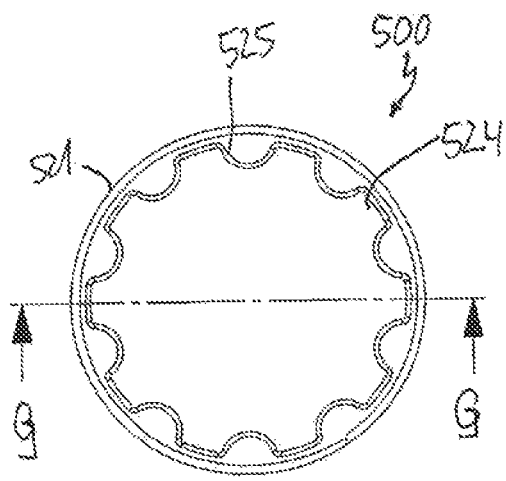
FIG. 33 shows a top view of a cover member of the bone plate shown in FIGS. 27 and 28.
Figure 34:
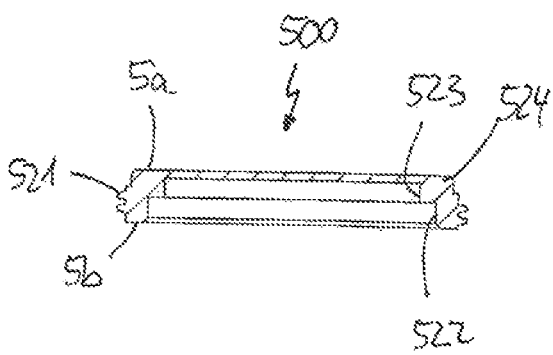
FIG. 34 shows a cross-sectional view of the cover member of FIG. 33 along line G-G in FIG. 33.

As illustrated in particular in FIGS. 27, 31 and 32, the disk 300 has a top side 3a and an opposite bottom side 3b and a substantially circular contour. A first portion 310 adjacent to the top side 3a has a cylindrical outer shape. An outer diameter of the first portion 310 is smaller than an inner diameter of the through-hole 210 adjacent to the top side 2a of the plate member 201 such that a gap is provided between the threaded portion 221 of the through-hole 210 and the first portion 310 of the disk 300. The gap allows placement of a portion of the cover member 500 into the through-hole 210. The first portion 310 is followed by a cylindrical second portion 320 that has a greater outer diameter than the first portion 310 and that comprises an external threaded portion 321 to cooperate with the internal thread of the threaded portion 221 of the through-hole 210. The external threaded portion 321 comprises a single thread turn or at least a portion of a single thread turn, or several thread turns. In order to accommodate the second portion 320 in the non-threaded portion 220 of the through-hole 210, the axial length of the second portion 320 should be kept small which means that a single thread turn may be sufficient.

Between the second portion 320 and the bottom side 3b there is a tapered outer portion 330 narrowing towards the bottom side 3b. The tapered portion 330 is configured to rest on the tapered lower portion 250 of the through-hole 210. As in the bone plate 1 described above, the shape of the contact surfaces is not limited to a tapered shape. Any shapes that are matching are possible.

The disk 300 further comprises an elongate slot 340 that extends completely through the disk 300 from the top side 3a to the bottom side 3b. The elongate slot 340 has two opposite long sides and two opposite short sides. A center of the elongate slot 340 in the longitudinal direction of the elongate slot 340 is arranged substantially at the center of the disk 300. Adjacent to the top side 3a, the elongate slot 340 comprises a widening section 340a that widens towards the top side 3a. Between the bottom side 3b and the widening section 340a, a seat portion 340b is provided that has a substantially spherical segment-shaped cross-section in a direction perpendicular to the longitudinal axis l of the disk 300. The seat portion 340b is configured to accommodate the head 42 of the bone anchor 4 as in the bone plate 1 described above. The width of the elongate slot 340 at a bottom of the seat portion 340b is smaller than the width of the head 42 of the bone anchor 4 but greater than a diameter of the shank 41 so that once the bone anchor 4 has been inserted into the bone, the bone plate 101 is temporarily fixed by the bone anchor 4 and cannot be removed. As in the previous embodiments, the seat portion 340b does not need to be spherically shaped but can have any other shape that prevents removal of the bone plate 101 after insertion of the bone anchor 4. The elongate slot 340 is configured to provide guidance for a displacement of the bone plate 101 along the longitudinal axis l relative to the bone anchor 4 once the bone anchor 4 is inserted into the elongate slot 340.

At opposite sides of the long sides of the elongate slot 340, two engagement recesses 350 that may have a circular inner contour are provided. The engagement recesses 350 are configured to be engaged with a tool (not shown) for inserting and/or rotating the disk 300 in the plate member 201. The engagement recesses 350 can have various other shapes and can be located at other positions. Only one engagement recess may also be sufficient.

Figure 35:
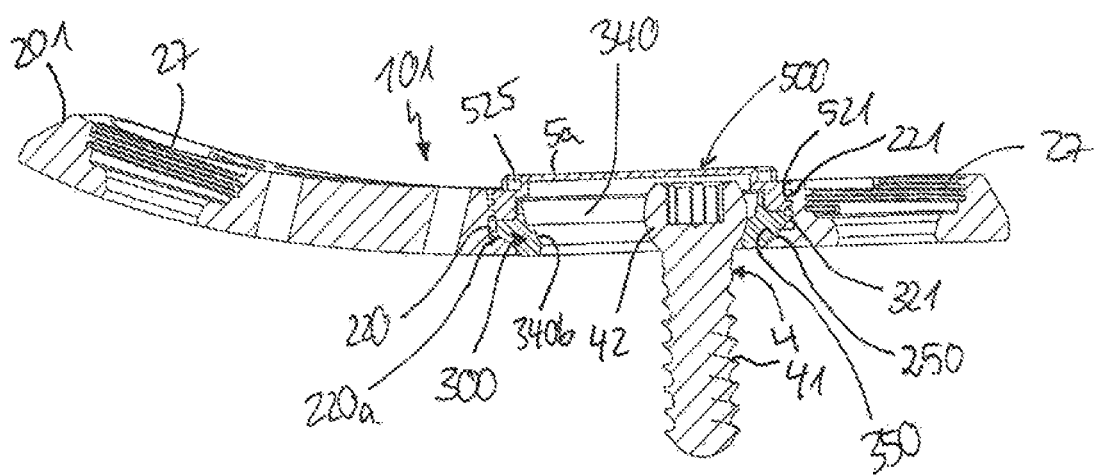
FIG. 35 shows a cross-sectional view of a bone plate assembly including the bone plate of FIGS. 27 and 28 in an assembled state.

A height of the disk 300 may preferably be such that once the disk 300 has been inserted into the through-hole 210 and rests on the support surface of the tapered portion 250 of the through-hole 210, the top side 3a does not project above the top side 2a of the plate member 201, as depicted in FIG. 35.

Next, the cover member 500 will be described with particular reference to FIGS. 27, 28, and 33 to 35. The cover member 500 is a substantially cylindrical member with a top side 5a and an opposite bottom side 5b. An outer threaded portion 521 is provided that is configured to cooperate with the threaded portion 221 of the through-hole 210. The top side 5a is closed. From the bottom side 5b, a first cylindrical recess 522 extends towards the top side 5a, which is followed by a second cylindrical recess 523 with a smaller inner diameter. The diameter of the first cylindrical recess 522 is such that when the cover member 500 is screwed into the threaded portion 221 of the through-hole 210, the cover member 500 enters into the gap between the inner wall of the through-hole 210 and the first portion 310 of the disk 300, as depicted in FIG. 35. Between the top side 5a and the outer threaded portion 521, an upper portion 524 with a reduced maximum outer diameter compared to the outer threaded portion 521 is formed that has a plurality of engagement recesses 525 extending in a radial direction. The contour of the engagement recesses 525 is shown as cylinder segment-shaped. However, any other contour suitable for being engaged with a tool may also be possible. The number of the engagement recesses 525 can vary. The more of the engagement recesses 525 that are present, the easier it is to remove the cover member 500, as there are several positions for an instrument to engage the cover member 500.

The height of the cover member 500 is such that when the cover member 500 is inserted into the through-hole 210, the upper portion 524 comprising the engagement recesses 525 slightly projects out of the top side 2a of the plate member 201 so that the engagement recesses 525 can be easily engaged by a tool. When the cover member 500 is screwed into the plate member 201, the bottom 5b of the cover member 500 comes into contact with the upper side of the second portion 320 of the disk 300 and presses thereupon to fix the disk 300.

The bone plate 101 is assembled as follows. First, the disk 300 is screwed into the through-hole 210 until the outer threaded portion 321 enters into the non-threaded portion 220 and the tapered portion 330 rests on the tapered portion 250. In this condition, the disk 300 is freely rotatable relative to the plate member 201. The bone plate 101 can then be used in the same manner as described above for the bone plate 1. After the final position of the bone plate 101 has been found and the bone plate 101 has been fixed to the bone or bone parts to be stabilized, the cover member 500 can be screwed into the through-hole 210 until the bottom side 5b abuts against the upper portion of the second portion 320 of the disk 300, as depicted in FIG. 35. Thereby, the cover member 500 prevents backing out of the bone anchor 4. Simultaneously, the disk 300 is fixed in its rotational position because the cover member 500 presses onto the disk 300. The cover member 500 protects the head 42 of the bone anchor 4 as it prevents ingrowth of bone material, vessels, or tissue around the head 42 of the bone anchor 4. This may be advantageous in a case where the bone plate 101 is intended to be removed after healing of the bone. For removing the bone plate 101, the cover member 500 is unscrewed and the bone anchor 4 can then also be unscrewed.

In an alternative manner of use, after implantation of the bone plate 101, bone material, such as bone graft, is filled into the slot 340 around the head 42 and, thereafter, the cover member 500 is screwed into the through-hole 210. Thereby, the ingrowth of the bone plate 101 can be promoted in a case where the bone plate 101 shall remain in the body. In a case where the bone anchor 4 is loosened for some reason, the disk 300 remains nevertheless fixed by the cover member 500.

While a threaded connection is shown between the disk 300 and the plate member 201, a similar advancement structure can also be used, such as, for example, a bayonet structure. While a threaded connection is shown between the cover member 500 and the plate member 201, another connection is also possible, for example, also a bayonet connection.

It shall be noted that it is conceivable to limit the rotational movement of the disk relative to the plate member with other means. For example, the outer shape of the disk and the inner contour of the through-hole may have other non-matching shapes that provide an abutment when rotating the disk relative to the plate member to limit the range of rotational movement.

Modifications of the embodiments described are conceivable. To realize the loss-proof arrangement of the disk in the plate member, it is also possible to provide instead of the projections and recesses that engage each other, an outer thread on the disk and an inner thread in the through-hole. Such a thread may have only a minimum number of thread turns, for example only one half turn. The disk can then be screwed into the through-hole through the first portion until the disk reaches the groove and the threads disengage.

The elongate slot can have various shapes and contours, for example, an L-shaped contour, a wavy contour or any other contour that might fulfill the same purpose.

It is also conceivable that the axis of the through-hole is inclined with respect to the top side and/or the bottom side of the plate member.

The plate member can have any shape. The top side and the bottom side need not be parallel. The plate member can have various thicknesses, and can be bent or otherwise shaped.

While only one single disk and corresponding through-hole was shown, it is also conceivable to have more than one disk and through-hole for further options of adjustment.

For the bone anchor, all kinds of bone anchors may be used, such as screws, nails, or pegs, all with or without cannulation. The head of the bone anchor may have any shape that is suitable to be guided by the slot. The head and the shank of the bone anchor may be separate parts that can be connected to each other, so that it is possible to first insert the shank into the bone, then place the bone plate onto the bone and thereafter connect the head to the shank.

It is also to be understood that the features of the different embodiments described herein are not limited to only these embodiments but can be mixed and matched to provide a plurality of still further embodiments.

What is claimed is:

1. A bone plate, comprising:
    a plate member including a top side, a bottom side, and a through-hole extending through the top side and the bottom side; and
    a disk, wherein the disk is receivable in the through-hole to be rotatably supported in the plate member about an axis of rotation extending from the top side to the bottom side, wherein the disk can be rotated 360° in the through-hole,
    the disk including a slot configured to receive a bone anchor having a head and a shank extending distal of the head therethrough, the slot defining a non-circular shape when viewed along the axis of rotation to allow a guided displacement of the bone plate relative to the bone anchor when the bone anchor is positioned in the slot in a plane perpendicular to the axis of rotation, and the slot having a widened upper portion and a lower seat portion narrower than the upper portion such that the disk at the slot is adapted to support the head of the bone anchor within the upper portion of the slot and above the lower portion of the slot and the lower portion of the slot is sized to pass the shank of the bone anchor,
    wherein the disk is receivable in the through-hole along a direction of the axis of rotation and is rotatable in the through-hole from a first position to a second position wherein the disk is configured to be held against removal from the through-hole along both directions of the axis of rotation when in the second position.

2. The bone plate of claim 1, wherein the slot is elongate with two opposite long sides and two opposite short sides.

3. The bone plate of claim 1, wherein the disk at where the slot is defined has at least a portion with a substantially spiral-shaped contour.

4. The bone plate of claim 1, wherein the disk has a substantially circular contour in a top view, and wherein the plate member comprises a support surface to support the disk.

5. The bone plate of claim 4, wherein the support surface is defined by an annular groove formed in a wall defining the through-hole.

6. The bone plate of claim 4, wherein the support surface is defined by an annular rim about a wall defining the through-hole.

7. The bone plate of claim 1, wherein the disk is secured in the through-hole against dislodgment.

8. The bone plate of claim 1, wherein the disk comprises at least one projection or recess at an outer surface of the disk configured to cooperate with at least one recess or projection at a wall around the through-hole such that the disk is insertable into the through-hole when the at least one projection or recess of the disk and the at least one recess or projection at the wall are aligned and the disk cannot be removed when the at least one projection or recess of the disk and the at least one recess or projection at the wall are not aligned.

9. The bone plate of claim 8, wherein the at least one projection or recess extends in a radial direction from the axis of rotation of the disk.

10. The bone plate of claim 1, wherein the disk comprises a portion which is deformable to engage a portion of the plate member to prevent removal of the disk while permitting rotation of the disk.

11. The bone plate of claim 1, wherein the slot comprises a seat to receive a head of a bone anchor.

12. The bone plate of claim 1, wherein the disk has a top side and a bottom side, and wherein the top side of the disk has at least one engagement recess for a tool.

13. The bone plate of claim 1, wherein the plate member includes at least one further through-hole configured to receive a further bone anchor.

14. The bone plate of claim 1, wherein an abutment is provided between the disk and an inner wall portion of the through-hole to limit a rotational movement of the disk relative to the plate member.

15. The bone plate of claim 1, further comprising a cover member configured to cover the disk in the plate member.

16. The bone plate of claim 15, wherein the cover member is attachable to the plate member.

17. The bone plate of claim 16, wherein the cover member is removable from the plate member.

18. The bone plate of claim 15, wherein the cover member is configured to engage the disk so as to fix a rotational position of the disk.

19. The bone plate of claim 18, wherein the disk is configured to be screwed into the through-hole.

20. The bone plate of claim 1, wherein a threaded portion is formed in a side wall of the through-hole.

21. The bone plate of claim 1, wherein the disk extends from a first side of the through-hole to a second side of the through-hole opposite the first side in a longitudinal direction of the plate member, and wherein the disk extends from a third side of the through-hole to a fourth side of the through-hole opposite the third side in a direction transverse to the longitudinal direction.

22. The bone plate of claim 1 in combination with the bone anchor, the head of the bone anchor is spherically shaped and seated in the upper portion of the slot and the shaft capable of being angled at a plurality of angles from within the lower portion of the slot.

23. A bone plate comprising:
a plate member including a top side, a bottom side, and a through-hole extending through the top side and the bottom side; and
a disk, wherein the disk is provided in the through-hole and rotatably supported in the plate member about an axis of rotation extending from the top side to the bottom side, the disk rotatable 360° in the through-hole, the disk including a slot configured to receive a bone anchor having a head and a shank extending distal of the head therethrough, the slot defining a non-circular shape when viewed along the axis of rotation to allow a guided displacement of the bone plate relative to the bone anchor when the bone anchor is positioned in the slot in a plane perpendicular to the axis of rotation and the slot having a widened upper portion and a lower seat portion narrower than the upper portion such that the disk at the slot is adapted to support the head of the bone anchor within the upper portion of the slot and above the lower portion of the slot and the lower portion of the slot is sized to pass the shank of the bone anchor.

24. A bone plate assembly comprising:
a bone plate comprising:
a plate member including a top side, a bottom side, and a circular through-hole extending through the top side and the bottom side; and
a disk, wherein the disk is receivable in the circular through-hole to be rotatably supported in the plate member about an axis of rotation extending from the top side to the bottom side, the disk including a slot, wherein the disk is receivable in the circular through-hole along a direction of the axis of rotation and is rotatable 360° in the through-hole independently of the plate member from a first position to a second position wherein the disk is configured to be held against removal from the circular through-hole along both directions of the axis of rotation when in the second position; and
a bone anchor insertable in the slot of the disk, the bone anchor having a head and a shank distal of the head, wherein the disk and the bone anchor are adapted to move relative to each other such as to allow a guided displacement of the bone plate in a plane perpendicular to the axis of rotation with respect to the bone anchor when the bone anchor is inserted in the slot, and the slot having a widened upper portion and a lower portion narrower than the upper portion, such that the disk at the slot is adapted to support the head of the bone anchor within the upper portion of the slot and above the lower portion of the slot and the lower portion of the slot is sized to pass the shank of the bone anchor.

25. A method of using a bone plate, the bone plate including a plate member including a through-hole, and a disk, wherein the disk is receivable in the through-hole to be rotatably supported in the plate member such that the disk can be rotated 360° independently of the plate member, the through-hole having a central axis, the disk including a slot having a widened upper portion and a lower portion narrower than the upper portion such that the disk at the slot is adapted to support the head of the bone anchor within the uvver portion of the slot and above the lower portion of the slot and the lower portion of the slot is sized to pass the shank of the bone anchor, the slot of the disk allowing a guided displacement of the bone plate with respect to the bone anchor in a plane perpendicular to the central axis, the method comprising:
placing the bone plate on a bone or a bone part;
inserting the bone anchor through the slot such that the head is supported by the disk within the upper portion of the slot and the shank extends through the lower portion of the slot; and then
rotating the disk in the through-hole in the range 0° to 360° about the central axis;
rotationally driving the bone anchor to fix the bone plate relative to the bone or the bone part.

26. The method of claim 25, further comprising displacing the bone plate with respect to the bone anchor in a plane perpendicular to the axis of rotation.

27. The method of claim 25, further comprising inserting the disk into the through-hole.

28. The method of claim 27, wherein inserting the disk into the through-hole comprises aligning at least one projection or recess at an outer surface of the disk with at least one recess or projection at wall around the through-hole.

29. The method of claim 25, further comprising inserting a cover member in the through-hole such that the cover member covers the disk.

30. A bone plate system, comprising:
a bone anchor having a spherically shaped head and a shank;
a plate member including a top side, a bottom side, and a through-hole extending through the top side and the bottom side; and
a disk, wherein the disk is receivable in the through-hole to be rotatably supported in the plate member about an axis of rotation extending from the top side to the bottom side,
the disk including a slot configured to receive the bone anchor, the slot defining a non-circular shape when viewed along the axis of rotation to allow a guided displacement of the bone plate relative to the bone anchor when the bone anchor is positioned in the slot in a plane perpendicular to the axis of rotation, and the slot having a widened upper portion and a lower seat portion narrower than the upper portion such that the disk at the slot is adapted to support the spherical-shaped head of the bone anchor within the upper portion of the slot and above the lower portion of the slot and the lower portion of the slot is sized to pass the shank of the bone anchor,
wherein the disk is receivable in the through-hole along a direction of the axis of rotation and is rotatable in the through-hole from a first position to a second position wherein the disk is configured to be held against removal from the through-hole along both directions of the axis of rotation when in the second position.

* * * * *